US011284824B2

(12) United States Patent
Crisfalusi et al.

(10) Patent No.: US 11,284,824 B2
(45) Date of Patent: Mar. 29, 2022

(54) METHOD AND SYSTEM FOR DETERMINING A HUMAN SOCIAL BEHAVIOR CLASSIFICATION

(71) Applicant: Everseen Limited, Blackpool (IE)

(72) Inventors: Dan Crisfalusi, Timis (RO); Alan O'Herlihy, Glenville (IE); Joe Allen, Ballybunion (IE); Dan Pescaru, Timisoara (RO); Cosmin Cernăzanu-Glăvan, Timisoara Timis (RO); Alexandru Arion, Timisoara (RO)

(73) Assignee: Everseen Limited, Blackpool (IE)

( * ) Notice: Subject to any disclaimer, the term of this patent is extended or adjusted under 35 U.S.C. 154(b) by 268 days.

(21) Appl. No.: 16/699,839

(22) Filed: Dec. 2, 2019

(65) Prior Publication Data
US 2021/0161451 A1    Jun. 3, 2021

(51) Int. Cl.
*A61B 5/16* (2006.01)
*G06F 3/01* (2006.01)
*G06V 40/16* (2022.01)

(52) U.S. Cl.
CPC .............. *A61B 5/167* (2013.01); *G06F 3/011* (2013.01); *G06V 40/174* (2022.01)

(58) Field of Classification Search
CPC combination set(s) only.
See application file for complete search history.

(56) References Cited

U.S. PATENT DOCUMENTS

| 5,850,352 A | * | 12/1998 | Moezzi | H04N 13/246 |
|---|---|---|---|---|
| | | | | 348/E13.058 |
| 6,678,413 B1 | * | 1/2004 | Liang | G06K 9/00335 |
| | | | | 382/181 |
| 7,930,204 B1 | * | 4/2011 | Sharma | G06Q 30/0203 |
| | | | | 705/7.32 |

(Continued)

FOREIGN PATENT DOCUMENTS

WO    2018194814 A1    10/2018

OTHER PUBLICATIONS

"Proper Use of TRACOM Brands." https://tracom.com/trademarks, Last visited on Dec. 20, 2019.

*Primary Examiner* — Motilewa Good-Johnson
(74) *Attorney, Agent, or Firm* — Young Basile Hanlon & MacFarlane, P.C.

(57) ABSTRACT

A system for assigning a social attribute class to a human subject in a predefined closed environment includes an image capturing component, a pose detection component configured to perform pose detection and tracking of a human subject in real-time, an action detection component configured to detect an action of the human subject, an activity detection component configured to relate a sequence of actions to detect an activity of the human subject, and a social attribute classification component. The social attribute classification component is configured to determine an average speed (s) of the human subject as a first social attribute, an interaction time of the human subject ($T_{int}$) as a second social attribute, an analysis time ($T_{anal}$) as a third social attribute, and automatically assigns a social attribute class to the human subject based on the values of the first, second and third social attributes.

20 Claims, 8 Drawing Sheets

(56) References Cited

U.S. PATENT DOCUMENTS

| | | | |
|---|---|---|---|
| 8,620,028 B2* | 12/2013 | Eaton | G08B 13/19613 |
| | | | 382/103 |
| 9,305,216 B1* | 4/2016 | Mishra | G06K 9/4604 |
| 9,996,736 B2 | 6/2018 | Smith et al. | |
| 10,198,818 B2* | 2/2019 | Varadarajan | G06T 7/73 |
| 10,339,775 B2* | 7/2019 | Robertson | G08B 13/19645 |
| 10,380,486 B2* | 8/2019 | Krauss | G06N 5/022 |
| 2014/0156645 A1* | 6/2014 | Brust | H04L 67/22 |
| | | | 707/722 |
| 2015/0006224 A1* | 1/2015 | Arditi | G06Q 10/06313 |
| | | | 705/7.23 |
| 2015/0242707 A1* | 8/2015 | Wilf | G06K 9/6256 |
| | | | 382/159 |
| 2016/0132788 A1* | 5/2016 | Li | G06Q 50/01 |
| | | | 706/12 |
| 2016/0275687 A1* | 9/2016 | Chu | G06T 7/0012 |
| 2017/0238846 A1 | 8/2017 | Xu et al. | |
| 2018/0018508 A1* | 1/2018 | Tusch | G06K 9/00771 |
| 2018/0096567 A1 | 4/2018 | Farrow et al. | |
| 2018/0101955 A1* | 4/2018 | Varadarajan | G06T 7/73 |
| 2021/0279475 A1* | 9/2021 | Tusch | G06K 9/00248 |

\* cited by examiner

METHOD AND SYSTEM FOR DETERMINING A HUMAN SOCIAL BEHAVIOR CLASSIFICATION

TECHNICAL FIELD

The present disclosure relates generally to a retail store environment, and more specifically to classifying human social behavior in the retail store environment.

BACKGROUND

A social attribute is an observable behaviour, which relates to how one moves in the world, communicates, makes decisions and interacts with others. Thus, social attributes are readily detectable through observation of human behaviour at different points within an observable environment. Traditional advertising methods attempt to predict personality styles in order to optimise targeted advertising campaigns to customers. However, social attributes are quite different from personality styles. More specifically, personality style includes social attributes together with aspects of people that cannot be readily externally observed such as beliefs, feelings, morals and attitudes.

In a retail store environment, it may be required to accurately predict human subject personality style solely based on observed human behaviour in order to reduce theft, or in order to study customer buying behavior, display advertisements, or for the purpose of providing meaningful, rapid, real-time advice to a retailer. In such environments, the accuracy of an estimated social attribute is largely dependent on the duration for which a customer is observed therein. In particular, questionnaires or other questioning methods may be implemented to reveal the less visible aspects of a person's beliefs and feelings. However, implementing such additional questioning systems is costly. Furthermore, consumers are increasingly weary of being questioned in this manner.

In view of the above, there is a need for a system and method that overcomes the limitations of existing systems, and that facilitates study of customer behavior in a retail store environment in a less costly and intrusive manner for the customer.

SUMMARY

In an aspect of the present disclosure, there is provided a system for assigning a social attribute class to a human subject in a predefined closed environment. The system includes an image-capturing component configured to capture image and video data of the human subject in real-time. The system may further include a pose detection component configured to perform pose detection and tracking of the human subject in real-time by analysing the image and video data. The system may further include an action detection component configured to relate a sequence of poses detected by the pose detection component to detect an action of the human subject. The system may further include an activity detection component configured to relate a sequence of actions detected by the action detection component to detect an activity of the human subject. The system may further include a social attribute classification component configured to determine an average speed s of the human subject as a first social attribute, based on outputs of the pose detection, action detection, and activity detection components, determine an interaction time $T_{int}$ as a second social attribute, the interaction time being an average time spent by the human subject interacting with one or more other human subjects in the pre-defined closed environment, determine an analysis time $T_{anal}$ as a third social attribute, the analysis time being an average time spent by the human subject analysing an item, and automatically assign a social attribute class to the human subject based on the values of the first, second and third social attributes.

In another aspect of the present disclosure, there is provided a method for assigning a social attribute class to a human subject in a predefined closed environment. The method includes capturing image and video data of the human subject in real-time. The method may further include performing pose detection and tracking of the human subject in real-time by analysing the image and video data. The method may further include detecting an action of the human subject by relating a sequence of detected poses. The method may further include detecting an activity of the human subject by relating a sequence of detected actions. The method may further include determining an average speed s of the human subject as a first social attribute, based on the pose detection, action detection, and activity detection. The method may further include determining an interaction time $T_{int}$ as a second social attribute, the interaction time being an average time spent by the human subject interacting with one or more other human subjects in the pre-defined closed environment. The method may further include determining an analysis time $T_{anal}$ as a third social attribute, the analysis time being an average time spent by the human subject analysing an item. The method may further include automatically assigning a social attribute class to the human subject based on the values of the first, second and third social attributes.

In yet another aspect of the present disclosure, there is provided a computer programmable product for assigning a social attribute class to a human subject in a predefined closed environment. The computer programmable product comprises a set of instructions, the set of instructions when executed by a processor causes the processor to capture image and video data of the human subject in real-time, perform pose detection and tracking of the human subject in real-time by analysing the image and video data, detect an action of the human subject by relating a sequence of detected poses, detect an activity of the human subject by relating a sequence of detected actions, determine an average speed s of the human subject as a first social attribute, based on the pose detection, action detection, and activity detection, determine an interaction time $T_{int}$ as a second social attribute, the interaction time being an average time spent by the human subject interacting with one or more other human subjects in the pre-defined closed environment, determine an analysis time $T_{anal}$ as a third social attribute, the analysis time being an average time spent by the human subject analysing an item, and automatically assign a social attribute class to the human subject based on the values of the first, second and third social attributes.

Various embodiments of the present invention provide a real-time classification of the social attribute class of an individual customer within a given retail environment. More specifically, the invention provides a real-time estimation of the social attribute classification of each customer within the field of view of a substantially overhead camera within a retail store area. This enables retailers to take rapid, responsive, and possibly pre-emptive action to adjust the retail environment proximal to a customer, and thereby provide a customized retail experience for the customer. However, it will be understood that the methodology adopted in the present invention is not restricted to a retail environment. On the contrary, the present invention is based on an understanding of behaviors manifested by humans in many different environments. Thus, the present invention is potentially applicable to any environment in which substantially undisturbed human behavior may be observed.

In another aspect, the present invention enables observation of customer behavioral attributes sufficient to enable estimation of social attributes, with minimal hardware outlay and minimal intrusion on a customer's privacy and associated customer disruption. By observing the customers without disturbance or interference, the present invention enables detection of unaffected social attribute typologies, thereby providing the retailer with an otherwise uncontaminated understanding of their customers, to use in designing appropriate environmental influences to enhance customer uptake of the required advertising message. Also, there is provided a mechanism for classifying human social attributes in real time during a trip to the store, and not requiring the storage of customer information from previous trips. This facilitates accommodating the context-sensitivity of the subject's social attribute, and avoiding the data protection and logistical challenges posed by the storage of personal data of individual customers.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF ILLUSTRATIVE EMBODIMENTS

The following detailed description illustrates embodiments of the present disclosure and ways in which they can be implemented. Although the best mode of carrying out the present disclosure has been disclosed, those skilled in the art would recognize that other embodiments for carrying out or practicing the present disclosure are also possible.

Figure 1:
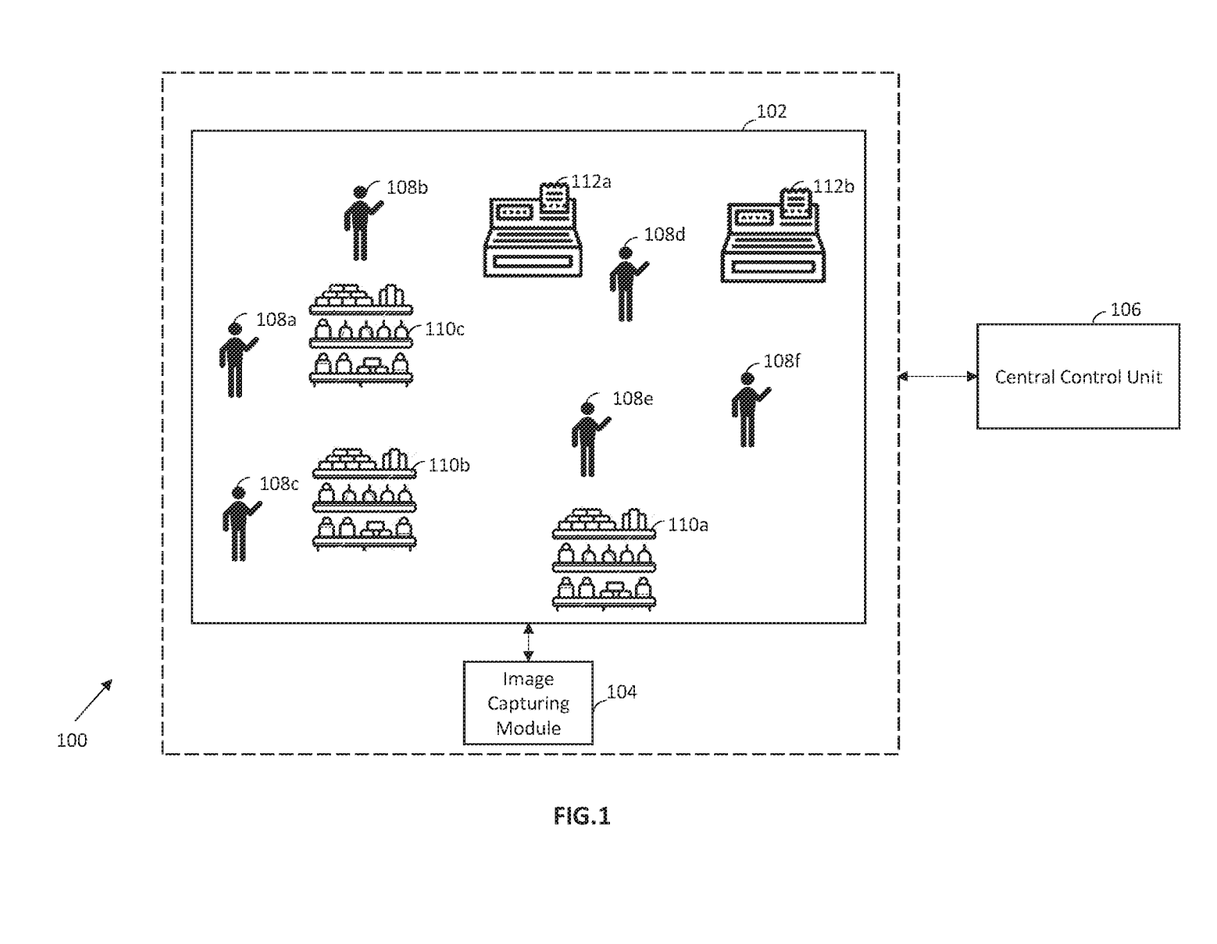
FIG. 1 illustrates an environment, wherein various embodiments of the present invention can be practiced.

FIG. 1 illustrates an environment 100, wherein various embodiments of the present invention can be practiced. The environment 100 includes a retail store area 102, an image capturing component 104 for capturing image and video data pertaining to the retail store area 102 in real time, and a central control unit 106 communicatively coupled to various computing devices present in the retail store area 102, and to the image capturing component 104 for classifying and studying the behaviour of the customers in the retail store area 102.

The retail store area 102 includes first through sixth customers 108a, 108b, 108c, 108d, 108e, and 108f (hereinafter collectively referred to as customers 108) first through third shelves 110a, 110b and 110c (hereinafter collectively referred to as shelves 110) that are configured to store items for purchase by the customers 108, and first and second billing counters 112a and 112b (hereinafter collectively referred to as counters 112) to enable the customers 108 to bill their products. A customer may be hereinafter also referred to as a subject.

While the present invention is directed to a retail store area 102, where the end goal of the customer relates to assessing and choosing a product, it is understood that in other environments an observed subject may have another aim.

In the context of the present disclosure, the counters 112 may be manually operated by a retail store executive, or self-operated by the customers 108 themselves. Each of the billing counters 112 may be equipped with a scanner for enabling a corresponding customer to scan one or more items themselves, and a user display for enabling a user to make a requisite selection and payment of one or more items. In an example, the scanner may be a bar code scanner for scanning bar code of an item, for identifying the item thereof. Preferably, the scanner is a stationary wall or table-mounted scanner, designed for check-out counters of supermarkets, and other retail stores, for scanning items placed in a scanning zone. In the context of the present disclosure, the scanning zone is an area in front of the scanner where the user brings up the items for scanning for the purpose of buying of those items. Each of the counters 112 may include a processor (not shown) for recording scanning of one or more items, and providing instructions on corresponding user display for payment of one or more scanned items.

The image capturing component 104 includes one or more cameras (not shown) installed in the retail store area 102 to capture image and video data thereof in real-time. In an embodiment of the present disclosure, the image capturing component 104 includes one or more overhead cameras. In another embodiment of the present disclosure, the image capturing component 104 includes one or more top down cameras. It would be apparent to one of ordinary skill in the art that the cameras of the image capturing component 104 may be positioned and angled in a plurality of ways at a sufficiently high altitude relative to the customer faces to enable multiple customers to be captured within the field of view of each camera, without necessarily capturing the features of the customer or each customer's face.

In an embodiment of the present disclosure, various computing devices of the retail store area 102 may be communicatively coupled to the central control unit 106 through a communication network. For example, the processor and scanner of each of the billing counters 112 may be communicatively coupled to the central control unit 106. The communication network may be any suitable wired network, wireless network, a combination of these or any other conventional network, without limiting the scope of the present disclosure. Some examples may include a Local Area Network (LAN), wireless LAN connection, an Internet connection, a point-to-point connection, or other network connection and combinations thereof. In one example, the network may include a mobile communication network, for example, 2G, 3G, 4G, or 5G mobile communication network. The communication network may be coupled to one or more other networks, thereby providing coupling between a greater number of devices. Such can be the case, for example, when networks are coupled together via the Internet.

In an embodiment of the present disclosure, the central control unit 106 is configured to classify and study behavior of the customers 108 according to a Merrill Reid social behavioral model. According to the work of Merrill and Reid, humans exhibit four potential social behavioral traits, categorized namely as extrovert, introvert, people oriented, and task oriented.

Figure 2:
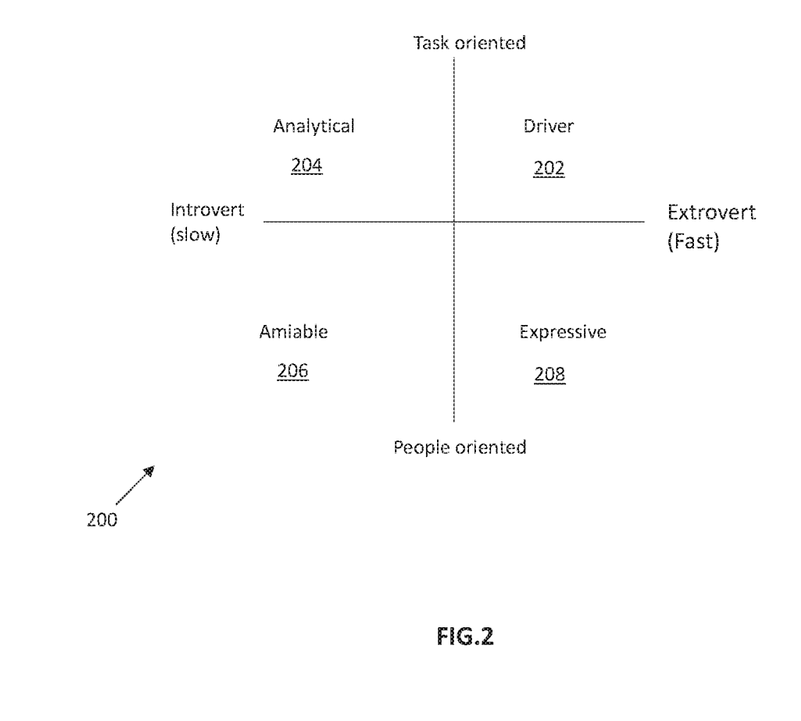
FIG. 2 illustrates a social behavioural space that illustrates four different types of social attribute classes amongst humans, in accordance with an embodiment of the present disclosure.

FIG. 2 illustrates a social behavioral space 200 that illustrates four different types of social attribute classes amongst humans, depending on the distribution of social behaviors within the social behavioral space 200. The first social attribute class 202 may be referred to as 'Driver', according to which a person is extroverted and task focused; and is characterized as being objective, focused, decisive, high energy and fast paced. The second social attribute class 204 may be referred to as 'Analytical' according to which a person is introverted and task focused; and is characterized as being fact and task oriented, logical, requiring evidence such as benchmarks and statistics, and needing time to decide. The third social attribute class 206 may be referred to as 'Amiable' according to which a person is introverted and people focused; and is characterized as consistent, dependable and stabilizing, cooperative and easy to get along with, indecisive and risk-averse. The fourth social attribute class 208 may be referred to as 'Expressive' according to which a person is extroverted and people focused; and is characterized as being relationship-oriented, verbally and socially adept, status conscious and a big-picture thinker.

It will be understood that the social attribute class manifested by a subject is susceptible to influence from external circumstances and stimuli, for example, whether the person is in a good mood, or the person is upset, or the person has other people accompanying them who may be distracting them etc. Thus, a social attribute classification of a given subject may vary in certain circumstances. However, once the external factor is no longer present, the subject's behavior may revert to its initial form.

It would be apparent to one of ordinary skill in the art, that several other human behavioral models such as theory of planned behavior, health belief model, transtheoretical model, and big five model may be used apart from the social attribute model described with reference to FIG. 2. Also, individual retailers may use their own customer classification models based on the above-mentioned human behavioral models, according to their business needs. While the present invention is described with reference to the detection of social attribute typologies, the person skilled in the art will understand that the present invention is not limited to this classification model. On the contrary, since the method of the invention relates to the detection of behaviorally important activities of each of a plurality of related or unrelated individuals, the method of the invention is operable with any behavioral classification model which relies on the detection of visually observable human activities.

Figure 3:
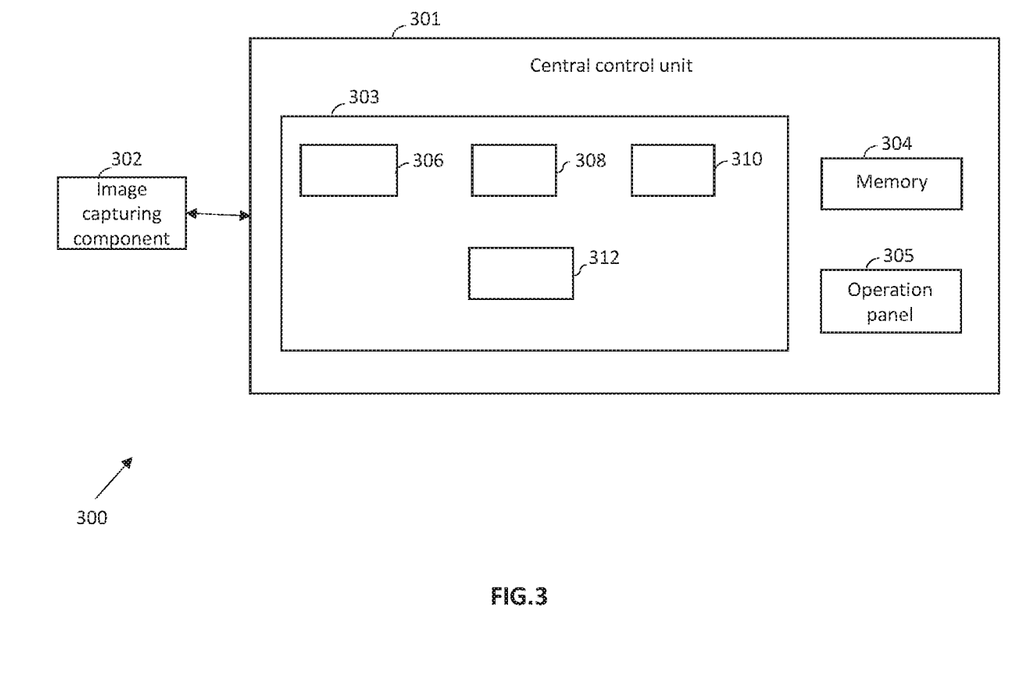
FIG. 3 illustrates a system for classifying and studying social human behavior, in accordance with another embodiment of the present disclosure.

FIG. 3 illustrates a system 300 for classifying and studying social human behavior, in accordance with an embodiment of the present disclosure. The system 300 includes a central control unit 301 (similar to the central control unit 106 of FIG. 1) and an image capturing component 302 (similar to the image capturing component 104 of FIG. 1). The central control unit 301 includes a central processing unit (CPU) 303, a memory 304 and an operation panel 305. The CPU 303 may include a processor, a microcontroller, or other circuitry that controls the operations of various components such as the operation panel 305, and the memory 304. The CPU 303 may execute software, firmware, and/or other instructions, for example, that are stored on a volatile or non-volatile memory, such as the memory 304, or otherwise provided to the CPU 303 for classifying and studying the behavior of the customers 108 in the retail area store 102. The CPU 303 may be connected to the operation panel 305, and the memory 304, through wired or wireless connections, such as one or more system buses, cables, or other interfaces. The operation panel 305 may be a user interface and may take the form of a physical keypad or touchscreen. The operation panel 305 may receive inputs from one or more users relating to selected functions, preferences, and/or authentication, and may provide and/or receive inputs visually and/or audibly.

In an embodiment of the present disclosure, the CPU 303 includes a pose detection component 306, an action detection component 308, an activity detection component 310, and a social attribute classification component 312. The pose detection component 306 is configured to perform the pose detection and tracking through analysis of video footage captured by the image capturing component 302 to ascertain the position of a subject's joints such as elbow, wrist, and head, at a given point in time. The pose detection component 306 may include convolutional neural networks (CNN) and dedicated logic elements for assessing the movements of the subject's joints over time, and detecting patterns associated with specific poses and tracking the subject's pose movements over time, for example, for distinguishing between right and left hands, and linking the joints according to a skeletal frame or sequences of joint movements associated with the adoption of specific poses. In an embodiment of the present disclosure, the image capturing component 302 may include multiple overhead cameras disposed at different angles, so to enable the pose detection component 306 to analyze specific aspects of the subject's skeletal anatomy, and perform motion estimation and movement prediction of different body part junctions.

The action detection component 308 is configured to use a dedicated logic element to relate a sequence of pose changes to a particular action such as picking a product from a shelf. More specifically, the action detection component 308 uses the pose variables detected by the pose detection component 306 in a recurrent neural network (RNN) to detect the pose changes made by the human subject from the video footage, and applies the logic element to identify from the corresponding action performed by the subject from detected pose changes.

The activity detection component 310 is configured to detect the presence of an observed sequence of actions determined by the action detection component 308 associated with the performance of a pre-defined task. In an example, item selection activity may include multiple actions such as picking up an item, moving item to shopping basket/trolley, and putting the item in the shopping basket/trolley. In an embodiment of the present disclosure, the activity detection component 310 may perform activity detection using a recurrent neural network or other classifier such as a single multi-layer classifier.

In an embodiment of the present disclosure, the classifiers and logic element used in the pose, action, and activity detection components 306, 308 and 310 may be trained based on pre-labelled video sequence employed in a supervised or semi-supervised learning methodology.

In an embodiment of the present disclosure, the social attribute classification component 312 is configured to observe behavioral traits of the customers using visual and other sensory inputs such as sound from the image capturing component 302. In another embodiment of the present disclosure, the social attribute classification component 312 is configured to observe behavioral traits using Artificial Intelligence (AI) to map out a behavioral type, and to personalize human interactive experience based on their behavioral type.

In yet another embodiment of the present disclosure, the social attribute classification component 312 is configured to observe behavioral traits of the customers 108 using attribute-based classification based on a few social attributes such as speed (s), interaction time ($T_{int}$), and analysis time ($T_{anal}$) of the customers 108. The speed attribute (s) includes an average speed of movement of the customers 108 within the retail store area 102; the interaction time attribute ($T_{int}$) is the average time spent by the customers 108 interacting with people or responding to a trigger, for example, in-store displayed adverts or alternative forced routes in the store or people welcoming customers at the entrance to the store; and the analysis time attribute ($T_{anal}$) includes the average time spent by the customers 108 in analyzing a product.

In an embodiment of the present disclosure, the social attribute classification component 312 determines the average speed (s) based on the output of the pose detection component 306, the action detection component 308, and the activity detection component 310. The average speed (s) attribute is calculated with reference to any kind of movement by the observed human subject, and does not consider the subject's time for responding to an external 'dangerous' stimulus, for example, a box falling from the shelf. More specifically, knowing the positions of a specific human subject's joints at given times from the video footage, the speed of movement of all the subject's joints, such as head, neck, shoulders, hands and feet may be determined over time. It is understood, that certain joints may be moved by the subject a lot faster than others, for example, hand movements may be much faster than torso or foot movements. Thus, the speed of movement of all the subject's joints are calculated and aggregated to obtain an overall estimate of the average speed of movement of the subject.

In an embodiment of the present disclosure, the process of aggregating the combined speeds of movements of the joints may include only including those joint movements whose speed exceeds a defined threshold. In another embodiment of the present disclosure, the process of aggregating may include using differential weightings on individual joints, such as obtaining a weighted average speed of overall joint movements. In yet another embodiment of the present disclosure, the process of aggregating may include evaluating particular actions separately from others, for example, weighting joint speeds associated with walking differently from hand movements in moving items on shelves.

In the context of the present disclosure, the interaction time attribute ($T_{int}$) is represented as:

$$T_{int} = f(T_{other}, T_{ear}, T_{face}) \tag{1}$$

Where, $T_{other}$=time spent by a subject in facing other people
($T_{ear}$)=time spent with the phone held to ear
($T_{face}$)=time spent facing a phone, for example, reading or viewing their phone screen
f=a weighted summation or other mathematical operator Based on the equation (1), the social attribute classification component 312 measures the time spent facing other people ($T_{other}$) using an output of the pose detection component 306, combined with a threshold for selecting human interaction activities according to their duration. In an example, a short incidental encounter such as bumping into each other, and a longer conversation between people have different durations. It may also be useful to distinguish between the persons with whom the subject engages. For example, engagement with a shop assistant to obtain directions to a particular product may indicate a different intention to obtain the product than interactions with accompanying persons, such as family members of friends. It may be easy to distinguish shop assistants from family members if shop assistants wear a uniform or if other persons are wearing clothing which allows them to be readily distinguished from persons accompanying the subject.

Using an output of the pose detection component 306, the social attribute classification component 312 is configured to measure a time spent by the subject with the phone held to their ear ($T_{ear}$). In contrast with $T_{other}$, thresholding of individual incidents is not necessary for the calculation of $T_{ear}$, unless any such threshold is intended to exclude very short answers to some incidental received calls, which do not reflect a subject's deliberate intention to interact with the phone.

The social attribute classification component 312 is configured to measure the time spent by the subject facing a phone ($T_{face}$) using an output from the pose detection component 306, and an object recognition process to identify the presence of phone. The object recognition aspect of this variable is necessary to enable a distinction to be made between time spent by the subject facing a phone as opposed to time spent by the subject reading the label of a product.

The social attribute classification component 312 is configured to determine the analysis time attribute ($T_{anal}$) based on a combination of time spent by a subject looking at a product in the subject's hand, and time spent looking at the shelves. The analysis time attribute ($T_{anal}$) is determined by focussing on hand and arm joint movements to detect specified activities such as taking a product from a shelf, looking at the product, rotating the product to see the price tag or ingredients or other features of the product, and putting the product in a basket/trolley or putting the product back on the shelf. In an embodiment of the present disclosure, the analysis time attribute ($T_{anal}$) is determined by combining the outputs of the pose detection component 306, the action detection component 308, and the activity detection component 310, with one or more object recognition algorithms designed to distinguish between the different objects that may be held in a subject's hands. For example, distinguishing between a sales product, and the user's mobile phone. With this distinction, the time spent by the subject with items other than retail products in their hands is excluded.

It is to be understood, that the analysis time attribute ($T_{anal}$) focusses on the end-goal of the subject's activity rather than a given product. In other words, the analysis time ($T_{anal}$) is not restricted to observations of the subject's interactions with a specific product. Instead, the analysis time ($T_{anal}$) measures the duration of the subject's interaction with an observable aspect of the end-goal of the subject's activity.

Figure 4:
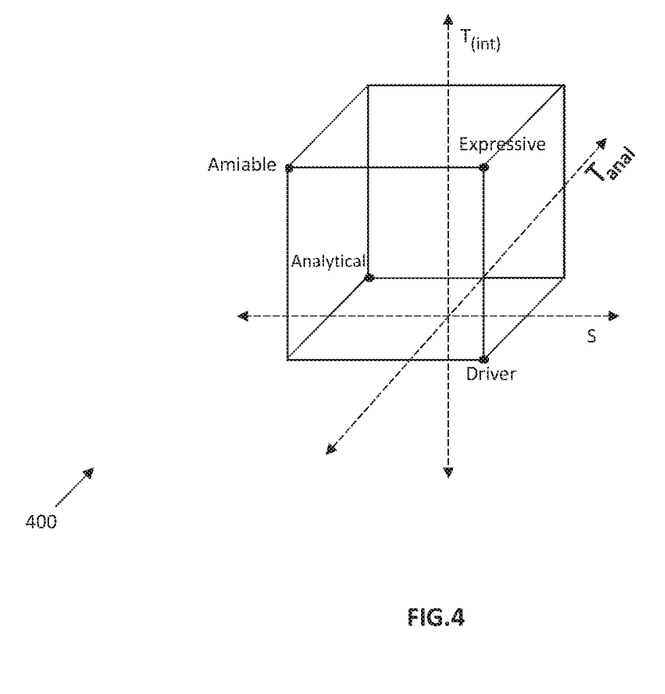
FIG. 4 illustrates an observable behavioral attribute space, in which the speed, average interaction time, and average analysis time form the x, y and z axis respectively, in accordance with an embodiment of the present disclosure.

FIG. 4 illustrates an observable behavioral attribute space 400, in which the speed s, interaction time $T_{int}$, and analysis time $T_{anal}$ attributes form the x, y and z axis respectively, and the four social attribute classes driver, expressive, amiable, analytical are indicated in the behavioral attribute space 400 based on corresponding values of the first, second and third attributes s, $T_{int}$, and $T_{anal}$.

As per the behavioral attribute space 400, the first social attribute class 'driver' exhibits a high s score, a low $T_{int}$ score, and a low $T_{anal}$ score. Further, the second social attribute class 'expressive' exhibits a high s score, a high $T_{int}$ score, and a low $T_{anal}$ score. Furthermore, the third social attribute class 'amiable' exhibits a low s score, a high $T_{int}$ score, and a low $T_{anal}$ score. Furthermore, the 'analytical' social attribute class exhibits a low s score, a low $T_{int}$ score, and a high $T_{anal}$ score.

It will be understood by the person skilled in the art that the present invention is not limited to measurements of the above-mentioned s, $T_{int}$ and $T_{anal}$ variables. On the contrary, the present invention is adaptable to use any variables (and any number of such variables) that may be calculated based on observations of a given human subject with each element of the retail store area 102. Similarly, since the present invention is operable with any behavioral model, the person skilled in the art will understand that the present invention is not limited to the above presentation and classifications based on the s, $T_{int}$ and $T_{anal}$ variables.

In an embodiment of the present disclosure, a sample measurement of the social attributes may be made for a statistically random set of at least 1000-5000 customers, to calibrate the relationship between the first, second and third social attributes (s, $T_{int}$ and $T_{anal}$) and the social attribute classes.

In an embodiment of the present disclosure, a two-threshold approach may be used to distinguish between the potential social attribute classes of a given subject, in which two thresholds are established for each social attribute with the help of independent appropriately skilled human behaviour experts. The first attribute 'speed s' may have upper and lower valued thresholds $Th_s^{hi}$ and $Th_s^{lo}$. The second attribute 'interaction time $T_{int}$' may have upper and lower valued thresholds $Th_{T_{int}}^{hi}$ and $Th_{T_{int}}^{lo}$. Similarly, the third attribute 'analysis time $T_{int}$' may have upper and lower valued thresholds $Th_{T_{anal}}^{hi}$ and $Th_{T_{anal}}^{lo}$ respectively. It will also be understood that the above-mentioned thresholds can also be more finely-tuned according to the risk appetite of the retailer or advertiser for minimising classification errors. The calculated values of a social attribute which exceed corresponding higher-valued threshold for that social attribute may be classified as "high." Correspondingly, calculated values of the social attribute which are less than the lower-valued threshold for that social attribute may be classified as "low." The calculated values which are between the higher and lower valued thresholds for a given social attribute may be considered "uncertain."

The social attribute classification component 312 is configured to determine one of the value 'high,' 'low,' 'uncertain' for each social attribute of a subject. Based on the 'high,' 'low' and 'uncertain' values of the social attributes, and the behavioural attribute space 400, the social attribute classification component 312 assigns a social attribute class to the subject.

Figure 5:
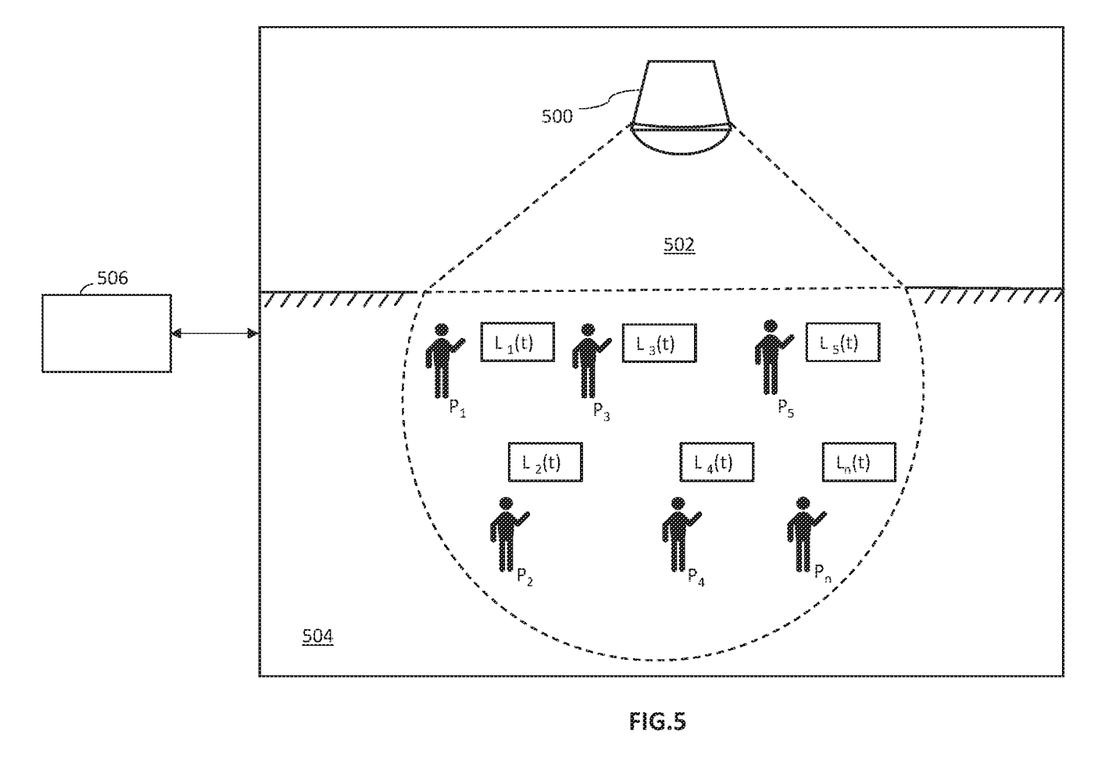
FIG. 5 illustrates an overhead camera positioned to capture a substantially top-down view of customers in the retail store area, in accordance with an embodiment of the present disclosure.

FIG. 5 illustrates a camera 500 positioned in an overhead manner and a field of view (FOV) 502 of the camera 500 to capture a substantially top-down view of the customers in the retail store area 504, in accordance with an embodiment of the present disclosure.

The FOV 502 includes n customers $p_1$ to $p_n$, i.e. $\underline{p} \in \mathbb{R}^n$, $\underline{p}=[p_1, p_2, \ldots p_n]^T$ in the monitored retail store area 504. In an embodiment of the present disclosure, the overhead camera 500 is communicatively coupled to a system 506 (similar to the system 300 of FIG. 3), so as to enable the system 506 to assign a social attribute class to each of the customers $p_1$ to $p_n$. The system 506 generates a set L of n labels for n customers, where $L \in \mathbb{R}^{n \times m}$, $L=[\underline{l}_1, \underline{l}_2, \ldots \underline{l}_n]^T)$, wherein each label includes a class score for each social attribute class, such that $\underline{l}_i \in \mathbb{R}^m$, $\underline{l}_i=[score_{dr}, score_{an}, score_{ex}, score_{am} \ldots l_m]$, where m is the number of social attribute classes. The class score could be a high/low binary indicator or could include analogue scores for each social attribute class. Based on these class scores and depending on a retailer's preferred behavioral model or decision criteria, the system 506 may assign a social attribute class to each customer within the FOV 502. The person skilled in the art would understand that these decision metrics are provided for example only, and in no way limit the scope of the present invention. In particular, the skilled person will understand that the invention is operable with any suitable decision criteria.

In another embodiment of the present disclosure, the system 506 is configured to perform real-time estimation of the social attribute class of n customers $p_1$ to $p_n$, i.e. $\underline{p} \in \mathbb{R}^n$, $\underline{p}=[p_1, p_2, \ldots p_n]^T$ in the monitored retail store area 504. This is achieved through the provision of real-time class scores for each social attribute class in the individual customer's label $\underline{l}_i(t)=[score_{dr}(t), score_{an}(t), score_{ex}(t), score_{am}(t) \ldots l_m(t)]$. The real-time labelling of social attribute class enables the retailer to obtain an evolving insight into the customer's social attribute classification and the effect of the customer's interactions with the other related or unrelated individuals in the same FOV 502. The real-time labelling of social attribute class further assists the retailer with real time interpretation of the effect of changing a customer's local environment from an individual customer perspective or a collective customer group-wise perspective. The real-time labelling of social attribute class further facilitates the retailer with rapid optimization of the customer's environment to maximize the sales outcome.

It may be noted that the accuracy of a given social attribute classification for a particular individual is at least partly dependent on the amount of time the individual is observed, and some considerable variations may be observed in the social attribute class scores when a studied individual first enters the FOV 502 of the camera 500. However, the social attribute class scores of the studied individual converge to a substantially settled state/value over time and without external intervention (e.g. $\Delta score_{dr} = |score_{dr}(t_i) - score_{dr}(t_{i-1})| \to 0$ as $i \to \infty$. Thus, the label for a given customer could also include an indication of the error in the estimated social attribute classification, where, for example the error could be expressed as the first derivative of the social attribute classification score.

Thus, the present invention also provides an estimate of the error in the provided real-time classification of each studied individual. Bearing in mind the potential cost to the retailer of adjusting a particular environmental condition, this aspect of the invention allows the retailer to establish thresholds for determining whether or not to take action, and thereby balance the costs of adjusting an environment variable against the risk of missing a sale to the observed customer.

However, the person skilled in the art will understand that the above expression for the error in the social attribute classification score is provided for example only, and in no way limits the scope of the invention to this expression. On the contrary, the skilled person would understand that the present invention is operable with any appropriate metric to express the error, including the time-varying error in a customer's social attribute classification.

In yet another embodiment of the present disclosure, the system 506 may be configured to obtain a more comprehensive insight into the customer's social attribute class, by essentially following the customer as they progress around the store and interact with different local environments in the store. The process of following a customer through a store may not require a specific detailed identification of a customer such as knowledge of their name, address, customer number. Instead, the process could be treated as crude session-based pattern recognition task such as detecting progression of a person with a given hair or clothing color between fields of view of proximal cameras, wherein the session represents the specific instance of the visit of the customer to that store. The system 506 may be configured to maintain consistent labelling of the customer during their stay in the store by detecting when a given customer enters the field of view of proximal cameras, using crude pattern recognition identification approach, and face recognition approach. The system 506 may assign a unique ID to each customer upon their entry in the retail store area 502 that may be maintained over the entire duration of the customer's stay in the retail store area 502, for example, during the customer's entire journey from the entrance of the store to exit from targeted area(s) of the store. The social attribute classes assigned to a customer may be computed at any given time using the entire history of attribute values observed up to that point in the customer's journey. If there are specific places with advertising panels in the store, the customer's social attribute classification may be determined every time the customer reaches a specific location in front of such panel. This procedure enables also refinement/correction of the social attribute classification if more than one advertising panel is present on a path of the customer.

Figure 6A:
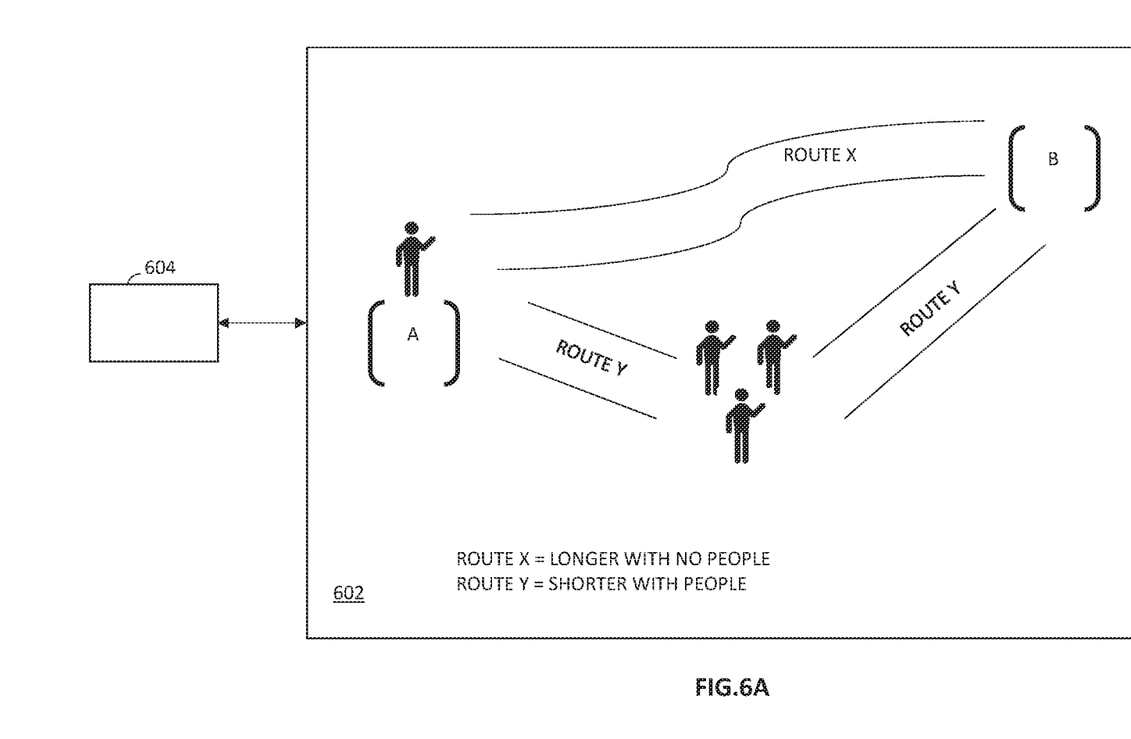
FIGS. 6A and 6B illustrate first, second and third routes x, y and z for the customers in the retail store area for facilitating social attribute classification, in accordance with an embodiment of the present disclosure.

FIG. 6A illustrates first and second routes x and y for the customers in a retail store area 602 for facilitating social attribute classification by a system 604 (similar to the system 300 of FIG. 3), in accordance with an embodiment of the present disclosure.

The system 604 is configured to assign a social attribute to a customer based on the route chosen by them. The first route x is longer, with no people and has a design which presents a very low possibility for human interaction, whereas, the second route y is shorter, with large number of people, and is designed with a very high probability of human interaction. Based on the path chosen, a customer may exhibit a preference which may partially classify them as having traits of either task-oriented or people-oriented. Also, the option to choose one of the first and second routes x and y may be implemented at an early contact stage with the customer, such as being near the entrance of the retail store, to force a determination early on, so as to facilitate the correct change in experience based on the derived mapping or to act as an early-stage classification which could be refined using the measured social attribute variables described above. Also, the distance covered per unit by the human subject may be used to determine the speed of movement of the human subject.

The system 604 is further configured to observe human subject by observing the amount of time the subject spends reading the label on a special offer shelf, examining the product and the care with which they either place the product in the basket or return the product to the display, and combine with previous results to indicate a particular personality style.

Figure 6B:
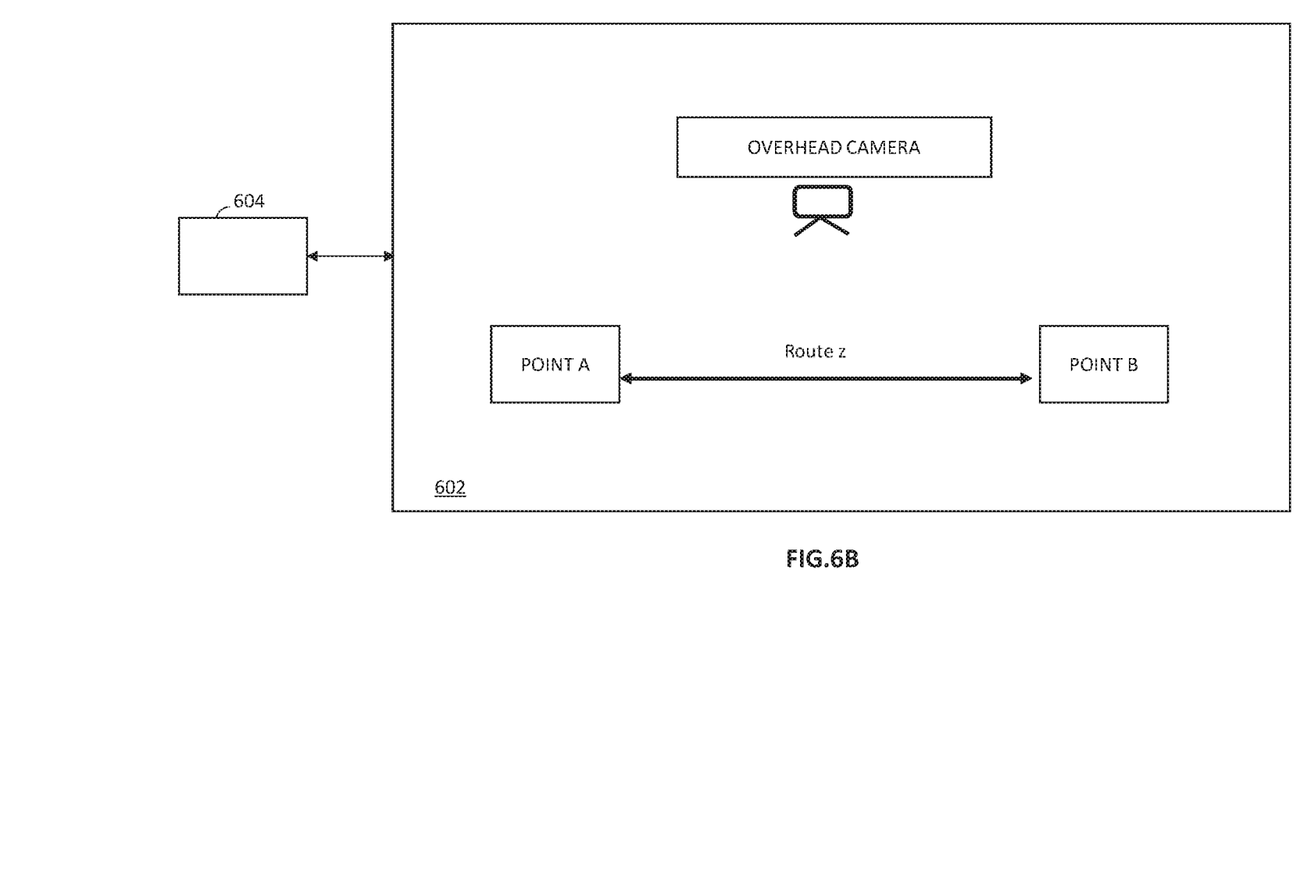

FIG. 6B illustrates a third route z for the customers in the retail store area 602 for facilitating social attribute classification. The system 604 may be configured to observe human behavior of the customers when they are asked to go through the third route z by offering free samples or other inducements. If the subject accepts the invitation, they may likely have an expressive or amiable (people oriented) social attribute class. To further distinguish between the social attribute classes, the subject could be offered further inducements to engage with the vendor in a manner which requires the customer to make themselves publicly visible. For example, the customer could be offered further free samples if they tag the product on Facebook, Instagram or other social media platform. If the subject accepts the invitation, then they are most likely to have an expressive social attribute class. Otherwise, the subject is most likely to have an amiable social attribute, because individuals with an amiable social attribute class do not typically enjoy public exposure.

Figure 7:
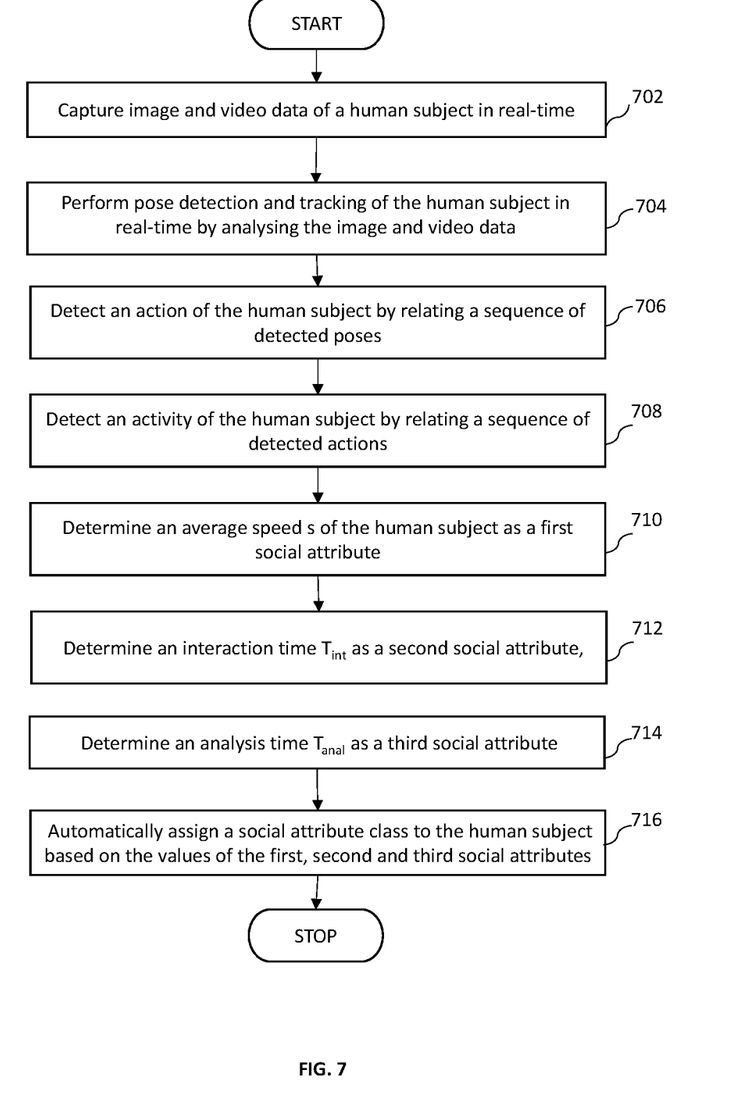
FIG. 7 is an illustration of steps of a method for classifying and studying social human behavior, in accordance with the present disclosure.

FIG. 7 is an illustration of steps of a method for classifying and studying social human behavior, in accordance with the present disclosure. The method is depicted as a collection of steps in a logical flow diagram, which represents a sequence of steps that can be implemented in hardware, software, or a combination thereof.

At step 702, image and video data of the one or more human subjects are captured in real-time. In an embodiment of the present disclosure, the image and video data may be captured using one or more overhead cameras that may be positioned and angled in a plurality of ways at a sufficiently high altitude relative to the customer faces to enable multiple customers to be captured within the field of view of each camera, without necessarily capturing the features of the customer's face.

At step 704, pose detection and tracking of a human subject in real-time is performed by analysing the image and video data. The pose detection is performed through analysis of video and image data to ascertain the position of a subject's joints such as elbow, wrist, and head, at a given point in time. The pose detection may be performed using convolutional neural networks (CNN) and dedicated logic elements for assessing the movements of the subject's joints over time, and detecting patterns associated with specific poses and tracking the subject's pose movements over time, for example, for distinguishing between right and left hands, and linking the joints according to a skeletal frame or sequences of joint movements associated with the adoption of specific poses.

At step 706, an action of the human subject is detected by relating a sequence of detected poses. The action detection may be performed using a dedicated logic element that relates a sequence of pose changes to a particular action such as picking a product from a shelf.

At step 708, an activity of the human subject is detected by relating a sequence of detected actions. The activity may be detected by detecting the presence of an observed sequence of actions associated with the performance of a pre-defined task. In an example, item selection activity may include multiple actions such as picking up an item, moving item to shopping basket/trolley, and putting the item in the shopping basket/trolley. In an embodiment of the present disclosure, the activity detection may be performed using a recurrent neural network or other classifier such as a single multi-layer classifier.

At step 710, an average speed s of the human subject, as a first social attribute is determined based on the pose detection, action detection, and activity detection. The average speed attribute (s) relates to any kind of intentional movement by the observed human subject, and does not consider the subject's time for responding to an external 'dangerous' stimulus, for example, a box falling from the shelf. More specifically, knowing the positions of a specific human subject's joints at given times from the video footage, the speed of movement of all the subject's joints, such as head, neck, shoulders, hands and feet may be determined over time. It is understood, that certain joints may be moved by the subject a lot faster than others, for example, hand movements may be much faster than torso or foot movements. Thus, the speed of movement of all the subject's joints are calculated and aggregated to obtain an overall estimate of the average speed of movement of the subject.

At step 712, an interaction time $T_{int}$ as a second social attribute is determined, the interaction time being an average time spent by the human subject interacting with one or more other human subjects in the pre-defined closed environment. In an embodiment of the present disclosure, the interaction time attribute is determined based on the time spent by the human subject in facing other human subjects, time spent with the phone held to their ear, and time spent facing their phone. The time spent facing other human subject is determined based on pose detection, and a time threshold for selecting an human interaction activity based on its corresponding duration. The time spent by the subject with the phone held to their ear is determined based on pose detection, and wherein the time spent by the human subject facing a phone is determined using pose detection, and an object recognition process to identify a presence of the phone.

At step 714, an analysis time $T_{anal}$ as a third social attribute is determined, the analysis time being an average time spent by the human subject analysing an item. In an embodiment of the present disclosure, the analysis time is determined by combining the outputs of the pose detection, the action detection, and the activity detection, with one or more object recognition algorithms configured to detect one or more objects held in a hand of the human subject.

At step 716, a social attribute class is automatically assigned to the human subject based on the values of the first, second and third social attributes. In an embodiment of the present disclosure, a social attribute class is assigned to the human subject from a group consisting of 'driver,' 'analytical,' 'amiable' and 'expressive'. In an embodiment of the present disclosure, a set of class scores is computed for the human subject, wherein the set includes first, second and third class scores for first, second and third social attributes respectively. Also, the social attribute class 'driver' has a high s score, a low $T_{int}$ score, and a low $T_{anal}$ score, the second social attribute class 'expressive' has a high s score, a high $T_{int}$ score, and a low $T_{anal}$ score, the third social attribute class 'amiable' has a low s score, a high $T_{int}$ score, and a low $T_{anal}$ score, and the fourth social attribute class "analytical" has a low s score, a low $T_{int}$ score, and a high $T_{anal}$ score.

Various embodiments of the present disclosure automatically identify and map out the social behavioral typology of a human subject based on their real time observed behavior in a particular environment. Thus, the present invention is potentially applicable to any environment in which substantially undisturbed human behavior may be observed. The outcome from the present invention may be used to tailor and optimize information delivery to a human in any environment where the human is required to receive and understand that information, and perhaps to make a decision based on that information. For example, the invention could be used to provide a real-time classification of the social attribute class of an individual customer within a given retail environment, wherein the results could be used to customize the delivery of advertisement material to a specific customer. More generally, the invention provides a mechanism of empowering marketeers by providing them with information about their customers, for example, enabling intelligent redesign of a store based on a better understanding of its customers. Similarly, the present invention could also be used for providing advice or instructions to employees, or identifying particularly nervous or agitated participants in stressful environments, for example, very nervous passengers in airport check-in, to enable more customized instruction-giving or other interaction with the relevant participants.

The classification of social attribute class provided by the present invention may be used in a system and method for optimizing the delivery of advertisement material, or otherwise optimizing a localized environment, for example, by way of alterations to lighting, music/sounds, smells, notices and displays, customer assistant presence etc. to an individual customer according to the attributes of the identified social attribute class of the customer. In keeping with the observation that the present invention is not restricted in its application to a retail environment, it should be understood that the social attribute classification provided by the present invention could be used to tailor and optimize information delivery to a human in any environment, where the human is required to receive and understand that information, and perhaps to make a decision or adopt a particular course of action based on that information.

Modifications to embodiments of the present disclosure described in the foregoing are possible without departing from the scope of the present disclosure as defined by the accompanying claims. Expressions such as "including," "comprising," "incorporating," "consisting of," "have," "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A system for assigning a social attribute class to a human subject in a predefined closed environment, the system comprising:

an image capturing component configured to capture image and video data of the human subject in real-time;

a pose detection component configured to perform pose detection and tracking of the human subject in real-time by analysing the image and video data;

an action detection component configured to relate a sequence of poses detected by the pose detection component to detect an action of the human subject;

an activity detection component configured to relate a sequence of actions detected by the action detection component to detect an activity of the human subject; and a social attribute classification component configured to:
  determine an average speed (s) of the human subject as a first social attribute, based on outputs of the pose detection, action detection, and activity detection components;
  determine an interaction time ($T_{int}$) as a second social attribute, the interaction time being an average of time spent by the human subject interacting with one or more other human subjects, time spent with a phone held to an ear of the human subject and time spent facing a phone of the human subject in the pre-defined closed environment;
  determine an analysis time ($T_{anal}$) as a third social attribute, the analysis time being an average time spent by the human subject analysing an item; and
  automatically assign a social attribute class to the human subject based on the values of the first, second and third social attributes.

2. The system of claim 1, wherein the image capturing component comprises one or more overhead cameras positioned at a high altitude relative to one or more customers to enable the one or more customers to be captured within a field of view of each camera.

3. The system of claim 1, wherein the time spent facing the one or more other human subjects is determined based on an output of the pose detection component, and a time threshold for selecting a human interaction activity based on corresponding duration, and wherein the time spent with the phone held to the ear is determined based on an output of the pose detection component, and wherein the time spent by the human subject facing the phone is determined using an output from the pose detection component, and an object recognition process to identify a presence of the phone.

4. The system of claim 1, wherein the analysis time is determined by combining the outputs of the pose detection component, the action detection component, and the activity detection component, with one or more object recognition algorithms configured to detect one or more objects held in a hand of the human subject.

5. The system of claim 1, wherein the social attribute classification component is configured to assign a social attribute class to the human subject from a group of social attribute classes consisting of driver, analytical, amiable AND expressive.

6. The system of claim 5, wherein the social attribute classification component is configured to compute a set of class scores for the human subject, the set including first, second and third class scores for first, second and third social attributes respectively.

7. The system of claim 6, wherein the first social attribute class driver has a high (s) score, a low ($T_{int}$) score, and a low ($T_{anal}$) score, the second social attribute class expressive has a high (s) score, a high ($T_{int}$) score, and a low ($T_{anal}$) score, the third social attribute class amiable has a low (s) score, a high ($T_{int}$) score, and a low ($T_{anal}$) score, and the fourth social attribute class analytical has a low (s) score, a low ($T_{int}$) score, and a high ($T_{anal}$) score.

8. The system of claim 5, wherein the social attribute classification component is configured to compute a set of class scores for the human subject in real-time, for assigning a social attribute class to the human subject in real-time, the set including first, second and third real-time class scores for first, second and third social attributes respectively.

9. The system of claim 1, wherein the social attribute classification component is configured to perform at least one of: crude session-based pattern recognition and facial recognition of the human subject for assigning a social attribute class to the human subject.

10. The system of claim 1, wherein the social attribute classification component is configured to automatically assign a social attribute class to the human subject based on a physical route chosen by the human subject while navigating the pre-defined close environment, and wherein a human subject that selects a short route including a large number of people is classified as people oriented, and wherein a human subject that selects an empty long route is classified as task oriented.

11. The system of claim 1, wherein the social attribute classification component is configured to determine behavioral traits of the human subject using Artificial Intelligence (AI) to map out a behavioral type, and to personalize a human interactive experience based on the behavioral type.

12. A method for assigning a social attribute class to a human subject in a predefined closed environment, the method comprising:
  capturing image and video data of the human subject in real-time;
  performing pose detection and tracking of the human subject in real-time by analysing the image and video data;
  detecting an action of the human subject by relating a sequence of detected poses;
  detecting an activity of the human subject by relating a sequence of detected actions;
  determining an average speed (s) of the human subject as a first social attribute, based on the pose detection, action detection, and activity detection;
  determining an interaction time ($T_{int}$) as a second social attribute, the interaction time being an average of time spent by the human subject interacting with one or more other human subjects, time spent with a phone held to an ear of the human subject and time spent facing a phone of the human subject in the pre-defined closed environment;
  determining an analysis time ($T_{anal}$) as a third social attribute, the analysis time being an average time spent by the human subject analysing an item; and
  automatically assigning a social attribute class to the human subject based on the values of the first, second and third social attributes.

13. The method as claimed in claim 12, wherein the time spent facing other human subject is determined based on the pose detection, and a time threshold for selecting an human interaction activity based on corresponding duration, and wherein the time spent with the phone held to the ear is determined based on the pose detection, and wherein the time spent by the human subject facing a phone is determined using the pose detection, and an object recognition process to identify a presence of the phone.

14. The method as claimed in claim 12, wherein the analysis time is determined by combining the outputs of the pose detection, the action detection, and the activity detection, with one or more object recognition algorithms configured to detect one or more objects held in a hand of the human subject.

15. The method as claimed in claim 12 further comprising assigning a social attribute class to the human subject from a group of social attribute classes consisting of driver, analytical, amiable AND expressive.

16. The method as claimed in claim 15 further comprising computing a set of class scores for the human subject, the set including first, second and third class scores for first, second and third social attributes respectively.

17. The method as claimed in claim 16, wherein the social attribute class driver has a high (s) score, a low ($T_{int}$) score, and a low ($T_{anal}$) score, the second social attribute class expressive has a high (s) score, a high ($T_{int}$) score, and a low ($T_{anal}$) score, the third social attribute class amiable has a low (s) score, a high ($T_{int}$) score, and a low ($T_{anal}$) score, and the fourth social attribute class analytical has a low (s) score, a low ($T_{int}$) score, and a high ($T_{anal}$) score.

18. The method as claimed in claim 15 further comprising computing a set of class scores for the human subject in real-time, for assigning a social attribute class to the human subject in real-time, the set including first, second and third real-time class scores for first, second and third social attributes respectively.

19. The method as claimed in claim 12, wherein the social attribute classification component is configured to automatically assign a social attribute class to the human subject based on a physical route chosen by the human subject while navigating the pre-defined close environment, and wherein a human subject that selects a short route including a large number of people is classified as people oriented, and wherein a human subject that selects an empty long route is classified as task oriented.

20. A computer programmable product for assigning a social attribute class to a human subject in a predefined closed environment, the computer programmable product comprising a set of instructions, the set of instructions when executed by a processor causes the processor to:
    capture image and video data of the human subject in real-time;
    perform pose detection and tracking of the human subject in real-time by analysing the image and video data;
    detect an action of the human subject by relating a sequence of detected poses;
    detect an activity of the human subject by relating a sequence of detected actions;
    determine an average speed (s) of the human subject as a first social attribute, based on the pose detection, action detection, and activity detection;
    determine an interaction time ($T_{int}$) as a second social attribute, the interaction time being an average of time spent by the human subject interacting with one or more other human subjects, time spent with a phone held to an ear of the human subject and time spent facing a phone of the human subject in the pre-defined closed environment;
    determine an analysis time ($T_{anal}$) as a third social attribute, the analysis time being an average time spent by the human subject analysing an item; and
    automatically assign a social attribute class to the human subject based on the values of the first, second and third social attributes.

* * * * *